(12) United States Patent
Davey et al.

(10) Patent No.: US 7,329,486 B2
(45) Date of Patent: *Feb. 12, 2008

(54) HIGH-THROUGHPUT ASSAY FOR VIRUS ENTRY AND DRUG SCREENING

(75) Inventors: Robert A. Davey, Galveston, TX (US); Andrey Kolokoltsov, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/813,383

(22) Filed: Mar. 30, 2004

(65) Prior Publication Data

US 2004/0191766 A1    Sep. 30, 2004

Related U.S. Application Data

(60) Provisional application No. 60/459,531, filed on Mar. 31, 2003.

(51) Int. Cl.
  *C12Q 1/70* (2006.01)
  *C12Q 1/66* (2006.01)
  *A61K 39/21* (2006.01)
(52) U.S. Cl. ............................ 435/5; 435/8; 424/207.1
(58) Field of Classification Search ...................... None
  See application file for complete search history.

(56) References Cited

U.S. PATENT DOCUMENTS

| | | | | |
|---|---|---|---|---|
| 4,593,002 A | * | 6/1986 | Dulbecco | .................. 435/91.41 |
| 5,916,563 A | * | 6/1999 | Young et al. | ............. 424/192.1 |
| 6,451,598 B1 | * | 9/2002 | Goldsmith et al. | .......... 435/334 |

FOREIGN PATENT DOCUMENTS

WO     WO 94/06920     *    3/1994

OTHER PUBLICATIONS

Blumenthal et al. Journal of Biological Chemistry. 1987; 262 (28): 13614-13619.*

* cited by examiner

*Primary Examiner*—Stacy B. Chen
(74) *Attorney, Agent, or Firm*—Benjamin Aaron Adler

(57) ABSTRACT

The present invention provides a rapid virus entry/binding detection assay. An enzyme such as luciferase was incorporated at the C-terminal end of viral envelope proteins that would deliver the enzyme into the viral particles upon viral assembly. Virus entry/binding can then be assayed by determining the enzymatic activities in infected cells. The assay allows high-throughput non-radioactive detection of virus entry within 30 minutes after virus-cell contact. This assay provides high signal to noise ratio and is useful for screening compounds that affect virus-cell binding and entry. The design also permits packaging of potential therapeutic proteins into functional virus particles and delivering them to specific cellular targets.

5 Claims, 8 Drawing Sheets

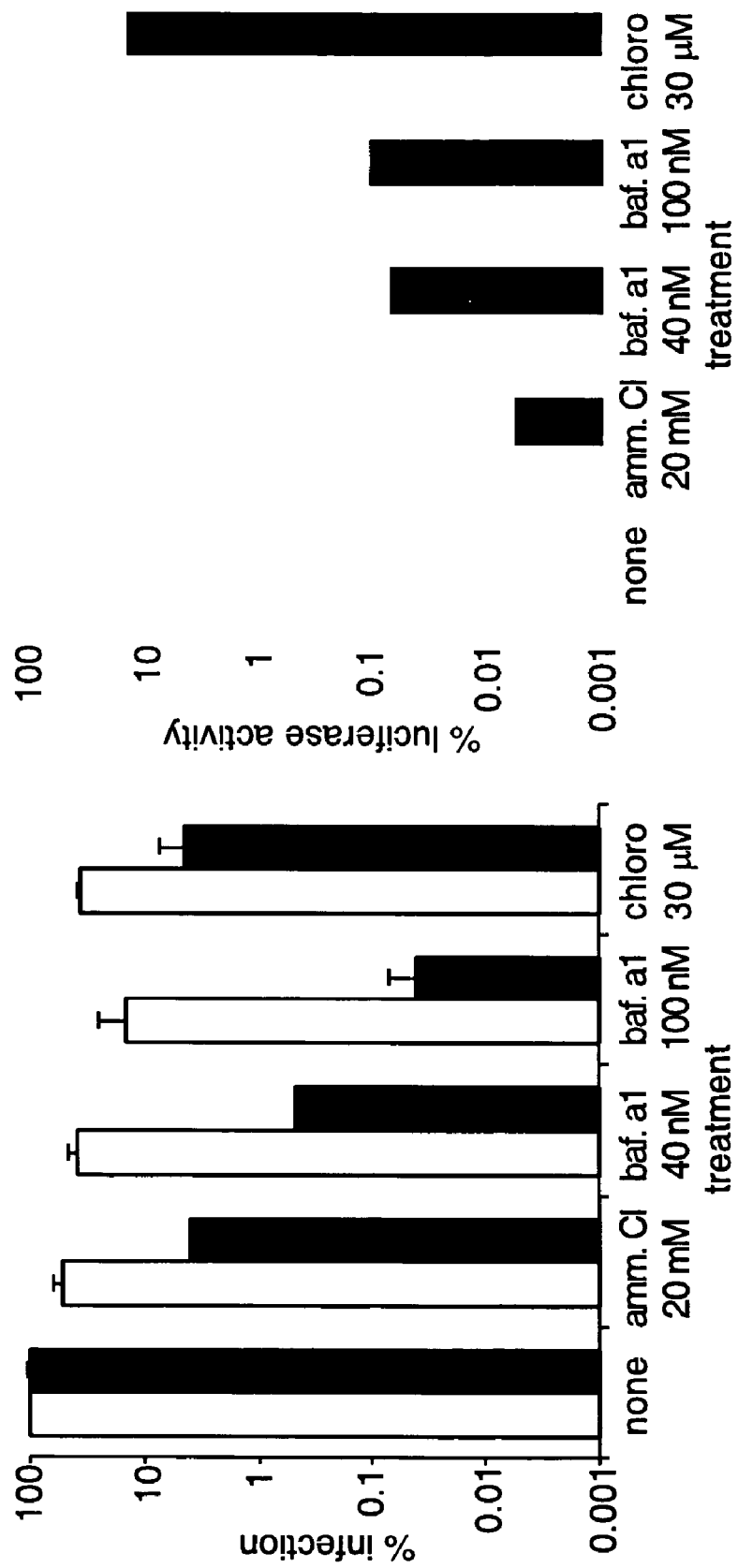

SEQUENCE LISTING

<160> NUMBER OF SEQ ID NOS: 6

<210> SEQ ID NO 1
<211> LENGTH: 30
<212> TYPE: DNA
<213> ORGANISM: artificial sequence
<220> FEATURE:
<221> NAME/KEY: primer_bind
<223> OTHER INFORMATION: Oligonucleotide sequence to modify 3' end
      of Friend57 MLV envelope gene to replace
      a native stop codon with EcoRV or EcoRI
      restriction endonuclease site.

```
<400> SEQUENCE: 1
ccatcgatta gttcaatttg ttaaagacag                              30

<210> SEQ ID NO 2
<211> LENGTH: 35
<212> TYPE: DNA
<213> ORGANISM: artificial sequence
<220> FEATURE:
<221> NAME/KEY: primer_bind
<223> OTHER INFORMATION: Oligonucleotide sequence to modify 3' end
      of Friend57 MLV envelope gene to replace
      a native stop codon with EcoRV or EcoRI
      restriction endonuclease site.

<400> SEQUENCE: 2
gatcgaattc tggctcgtat tctagtggtt ttagc                        35

<210> SEQ ID NO 3
<211> LENGTH: 35
<212> TYPE: DNA
<213> ORGANISM: artificial sequence
<220> FEATURE:
<221> NAME/KEY: primer_bind
<223> OTHER INFORMATION: Oligonucleotide sequence to modify firefly
      luciferase gene to gain EcoRV or EcoRI
      restriction endonuclease site at its 5' end.

<400> SEQUENCE: 3
gatcgaattc gaagacgcca aaaacataaa gaaag                        35

<210> SEQ ID NO 4
<211> LENGTH: 35
<212> TYPE: DNA
<213> ORGANISM: artificial sequence
<220> FEATURE:
<221> NAME/KEY: primer_bind
<223> OTHER INFORMATION: Oligonucleotide sequence to modify firefly
      luciferase gene to gain EcoRV or EcoRI site
      at its 5' end and two tandem stop codons
      and NotI site at its 3' end.

<400> SEQUENCE: 4
gatgcggccg cttacacggc gatctttccg ccctt                        35

<210> SEQ ID NO 5
<211> LENGTH: 4
<212> TYPE: PRT
<213> ORGANISM: artificial sequence
<220> FEATURE:
<223> OTHER INFORMATION: 4 amino acid residue in the spacer
      peptide between the envelope protein C-
      terminus and the luciferase N-terminus
      in env-luc2 construct.

<400> SEQUENCE: 5

Glu Phe Gly Ser

<210> SEQ ID NO 6
<211> LENGTH: 31
<212> TYPE: DNA
<213> ORGANISM: artificial sequence
<220> FEATURE:
<221> NAME/KEY: primer_bind
<223> OTHER INFORMATION: Sense strand oligonucleotide sequence for the
      T471P mutation.
```

```
<400> SEQUENCE: 6
cgccgcggga gtagggcccg gaactaccgc c                                      31
```

HIGH-THROUGHPUT ASSAY FOR VIRUS ENTRY AND DRUG SCREENING

CROSS REFERENCE TO RELATED APPLICATION

This non-provisional application claims benefit of provisional application U.S. Ser. No. 60/459,531, filed on Mar. 31, 2003, now abandoned.

BACKGROUND OF THE INVENTION

1. Field of the Invention

The present invention relates generally to the field of drug screening. More specifically, the present invention relates to high-throughput assays that measure virus entry and are useful for drug screening.

2. Description of the Related Art

A few entry inhibitors exist for influenza and HIV. While these inhibitors show some promise, they are far from perfect and have low efficacy. The discovery of similar but more effective drugs has been hindered by a lack of high-throughput, high signal to noise assay for screening lead compounds/drugs.

pH-dependent models such as influenza A and semliki forest virus have been used to study the mechanisms of enveloped virus entry. This is because it is possible to induce an en-masse fusion event by dropping the pH of the medium. Fluorescence dequenching or FRET assays are used to measure the kinetics of fusion in such viruses and have been used to understand the effects of mutations and anti-viral drugs (Blumenthal, R. et.al, 1987, Danieli, T., et.al., 1996). In this assay, the fluorescent probes incorporated in the virus membranes mix with and become diluted in the target cell or liposome membrane. The resulting change in the fluorescence gives a real-time measure of fusion. However, these entry assays cannot be applied easily to the pH-independent viruses since fusion events are infrequent, cannot be co-ordinated and the receptors are difficult to manipulate since they tend to be integral, multi-transmembrane span-containing proteins. In such studies, passive diffusion of the fluorophore contributes significantly to the signal and complex analysis of the data is required to observe signal due to fusion.

The need for more sensitive measurement of pH-dependent virus entry has therefore, led to the development of assays to detect cell-cell fusion, early genome replication events and assays that use recombinant viral protein-GFP fusions (Erlwein, O., et.al, 2003, McDonald, D., et.al, 2002, Spitzer, D., et.al, 2003). In cell-cell fusion assay, which is used to confirm the role of factors important in fusion, cells made to express the virus envelope proteins on the surfaces are labeled with one fluorophore and are mixed with target cells bearing receptor and second fluorophore. Fusion is measured by observing syncytia formation. Independent labeling of the cell membrane and cytoplasm provides information on membrane and cytoplasm mixing. However, syncytia formation is slow and does not correlate to infection kinetics. Additionally, in case of HIV, the chemokine receptor, Bonzo promotes syncytia but does not play any significant role in entry (Edinger, A. L., et.al. 1998, Sharron, M., et.al., 2000).

There are several assays that detect virus infection. Some assays measure infection by using the reporter gene expression in the infected cell. However, this is very complicated process. To obtain expression, a virus must penetrate the cell membrane, the core must be trafficked to the correct sub-cellular location, then the genome is exposed and finally the reporter is expressed. This requires for example in retroviruses, the cell to be at a specific stage and the gene expression requires at least 24 hours after contact with cells which is far removed from the initial entry event.

Other assays, which involve making virus-protein fusions to green fluorescent protein, have been useful to follow virus after it has entered the cell. The use of fluorescently labeled dUTP even permits the visualization of genomes undergoing reverse transcription (McDonald, D., et.al., 2002). However, these assays cannot be easily used to examine entry as cell bound virus cannot be differentiated from that which has just entered and for retroviruses, particle to infectious particle ratios typically exceed 10-100. This means that most viruses are either defective or trafficked to non-productive pathways within the cell.

Contents-mixing assays, which measure the release of virus contents into the cell or target vesicle, demonstrate the greatest potential for rapid measurement of virus entry. In case of retroviruses, this is most commonly done by viral DNA synthesis: transcripts can then be detected by PCR, typically around 4 hours after cell contact. However, it is not known at what point within this 4-hour window, the genome uncoating takes place and the assay is not quantitative.

A method where the enzyme β-lactamase is fused to the HIV protein, vpr (Cavrois, M., et.al., 2002) was developed recently to obtain quantitative data. Vpr is packaged into HIV particles as part of virus assembly and provided a means of targeting a marker enzyme into the particle. Caged substrate was perfused into cells to give signal. However, in practice, this assay lacked sensitivity since the detection of entry required 12 hours of cell culture for production of sufficient reaction product. To enable shorter measurement times, an MOI of more than 10-100 is required which is not physiological.

Thus, the prior art is deficient in assays that are fast, simple, physiological and sensitive to measure virus entry. The present invention fulfils this need by providing method that allows rapid and high-throughput non-radioactive detection of virus entry, has high signal to noise ratio and can detect virus entry into cells within 30 minutes after virus-cell contact.

SUMMARY OF THE INVENTION

The present invention allows rapid and high-throughput non-radioactive detection and quantitative assessment of virus entry. The method provides a signal to noise ratio of >100-1000 and can detect both pH-dependent and independent virus entry into cells within 30 minutes after virus-cell contact.

The method requires encapsulation of a sensitive reporter enzyme, luciferase, directly into fully infectious, intact viral particles. This is different from assays where a reporter gene is used. The virus envelope protein of a murine leukemia virus (MLV) was modified to have the luciferase enzyme at its C-terminus. FIG. 1 shows the envelope-luciferase (env-LUC) construct. Once incorporated into virus, the env-LUC construct was further processed by a viral protease (cleavage, FIG. 1) and the luciferase enzyme was released into the cytoplasm of the virus particle. This permits easy interaction with substrate (when required). Viruses were assembled by transfection of cells with the wild type envelope protein, the env-LUC construct and plasmids encoding virus structural proteins. Virus was then purified from culture supernatants or the crude medium can be used directly. Addition of virus-containing solutions to cells lacking receptor for the envelope protein gave no activity in the presence of substrate (luciferin). However, after a two-hour incubation with cells that have receptors to bind the viruses, signals typically exceeding 3,000 light units/second were observed. Although EDTA can effectively quench free luciferase activity, it did not diminish the signal. This indicated that the env-LUC construct had reached a compartment protected from EDTA and therefore, the assay is a read-out of virus entry.

While two hours was a typical incubation time in most of the assays, 30 minutes was adequate to see a strong signal. The assay can be performed in a 96-well plate using a luminometer capable of measuring this format. Using 10,000 cells per well, the signal: noise ratio was >1000 with the background subtracted and >10 without subtracting the noise in the instrument. On a better instrument this would not be an issue and the signal:noise ratio would be >1000. This indicates the assay can be used for high throughput drug screening.

The wild type envelope protein used in the assembly of virus is selected from the group consisting of murine leukemia virus, human immunodeficiency virus, retrovirus, Vesicular Stomatitis virus, Arenaviruses, Hanta virus, Ebola virus and Venezuelan Equine Encephalitis virus. Thus, this novel assay permits the measurement of entry of murine leukemia virus and pseudotypes with greater sensitivity and more rapidly than previously possible. Additionally, by controlling the amount of enzyme that is incorporated into each virus particle, it is possible to completely encapsidate the marker, thereby eliminating signal due to defective particles.

In addition to detecting the viral entry, the amount of cell-bound virus can be determined in the same assay by addition of detergents to expose luciferase. This was demonstrated when a virus carrying a mutation in the fusion peptide bound normally to cells but was unable to infect them and gave no signal. This assay also demonstrated that inhibitors of endosomal acidification inhibited signal from vesicular stomatitis virus pseudotypes but not murine leukemia virus, consistent with a pH-independent mode of entry for the later virus. Additionally, fusion kinetics of this assay is rapid, with a half-life of 25 minutes after a delay of 10-15 minutes.

In one embodiment of the present invention, there is provided a method of detecting virus binding and entry to target cell comprising the steps of creating an envelope-enzyme fusion protein by attaching an enzyme to the C-terminal end of a viral envelope protein. Virus particles comprising of the fusion protein and wild type envelope protein are generated and infect target cells. Activities of enzyme measured in such infected cells are measures of virus binding and entry to the target cells that are mediated by the wild type viral envelope protein.

In another embodiment of the present invention, there is a method of evaluating influence of amino acid substitutions on virus binding and entry comprising the steps of constructing a mutant containing the amino acid substitution in the viral envelope protein. The creation of mutant envelope-enzyme fusion protein, generation of virus particle comprising of wild type envelope protein and mutant fusion protein as well as infection of target cells is carried out in a manner as described earlier. Measurement of activities of the enzyme in the lysed and intact infected cells will enable the evaluation of amino acid substitution on virus binding and entry.

In still another embodiment of the present invention, there is a method for determining whether the viral entry mechanism is pH dependent comprising all the same steps as described earlier. However, in this case, the enzyme activities are measured in the absence and presence of the inhibitors of endosomal acidification where decreased enzyme activities in the presence of the inhibitors indicate that the virus has a pH-dependent mode of entry.

In a preferred embodiment of the present invention is a method of receptor-dependent targeted therapy to an individual. Such a therapy comprises the step of attaching a therapeutic protein to the C-terminal end of a viral envelope protein, thereby creating a fusion protein. Virus particles comprising said fusion protein and wild type viral envelope protein are then generated. Such a composition when administered to an individual mediates receptor-dependent targeted therapy to the individual.

In another embodiment of the present invention is a pharmaceutical composition comprising of therapeutic protein-containing virus.

The invention may also be described in certain embodiments to method for screening neutralizing antibodies in patients' sera. The creation of an envelope-enzyme fusion protein, generation of virus particles comprising of fusion protein and wild type viral envelope protein as well as infection of target cells in the patients' sera are carried out as described earlier. Measurements of enzyme activities in the infected cells of the sera, where decreased enzyme activities in the sera indicate that there are neutralizing antibodies in the sera.

In yet another embodiment of the present invention is a kit comprising (a) enzyme-containing virus pseudotypes and (b) substrate for that particular enzyme.

In still yet another embodiment of the present invention is a method of screening for compound that inhibits virus binding and entry to target cell. The creation of an envelope-enzyme fusion protein, generation of virus particle comprising of the fusion protein and wild type envelope protein as well as infection of target cells is carried out as described earlier. Measurement of enzyme activities in the infected cells where decreased enzyme activities in the presence of the compound indicate that the compound inhibits virus binding and entry to the target cells mediated by said wild type viral envelope protein.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 7 (FIGS. 7A, 7B (I, II), 7C) shows the design of the construct, production and optimization of MLV incorporating luciferase in the viral lumen. FIG. 7B (I, left panel) shows cell lysates and particles isolated by pelleting through a 20% sucrose cushion. FIG. 7B (II, right panel) shows lysate of cells transfected with plasmids encoding env (5 µg) or env+env-luc1 (4 and 1 µg respectively). The arrowhead indicates band of predicted size for env-luc fusion protein with size markers to the left.

FIG. 10 (10A and 10B) shows effect of endosomal acidification inhibitors on infection and luciferase entry-assay signal. Cells ($2 \times 10^6$ per sample) were treated with ammonium chloride (amm.Cl), bafilomycin a1 (baf. A1) or chloroquine (chloro) at 20 mM, 40 nM+100 nM and 30 µM, respectively, and then Friend MLV (open bars) or VSV-G (solid bars) pseudotyped virus encoding β-galactosidase and containing env-luc1 was applied. Half of the cells were plated and colonies counted after 2 days by staining for β-galactosidase activity (FIG. 10A, left panel). The remaining cells were assayed for luciferase activity (FIG. 10B, right panel) after 1 hour.

DETAILED DESCRIPTION OF THE INVENTION

Figure 1:
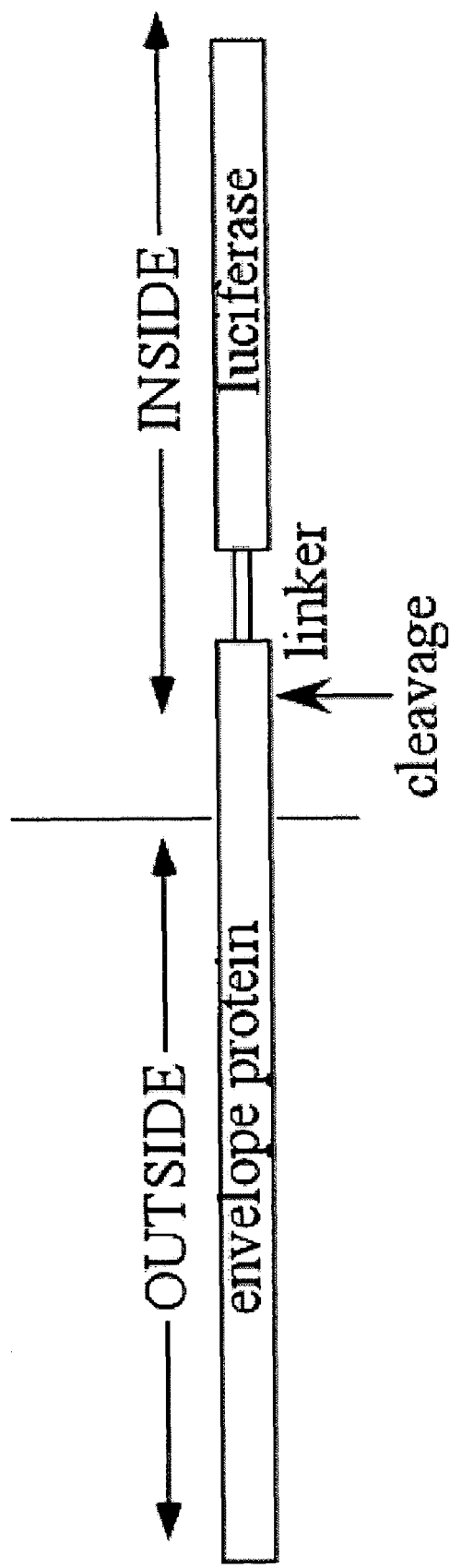
FIG. 1 shows envelope-luciferase construct.

In contrast to other assays that use a reporter gene, the assay of the present invention utilizes a reporter enzyme protein incorporated into the virus itself. In one embodiment, the virus envelope protein of a murine leukemia virus (MLV) was modified to have the luciferase enzyme attached at its C-terminus. FIG. 1 shows the envelope-luciferase construct. Once the construct is incorporated into virus, the envelope-luciferase construct is further processed by a viral protease (cleavage, FIG. 1). Consequently, the luciferase is released into the cytoplasm of the virus particle, thereby permitting easy assess and interaction with the substrate.

While luciferase was used here, as it has certain advantages for sensitivity, in practice any enzyme or protein could be attached in the same way. Examples of such are bacterial or placental alkaline phosphatase, b-galactosidase, fluorescent proteins such as Green fluorescent protein or toxins.

Viruses are assembled by transfection of cells with the wild type envelope protein, the envelope-luciferase construct and plasmids encoding virus structural proteins. A marker gene distinct from luciferase may be incorporated as well, although this is not necessary for this assay. Virus is then purified from culture supernatants or the crude medium can be used directly. Addition of virus-containing solutions to cells lacking virus receptor gives no enzyme activity in the presence of the substrate luciferin. In the presence of receptor positive cells, there was a dramatic increase in luciferase-associated activity within 15 minutes after incubation with virus particles. The signal was not diminished upon addition of EDTA, indicating that the envelope-luciferase construct had reached a compartment protected from EDTA and the virus must have been internalized or entered at the cell surface.

Generally, signals exceeding 3,000 light units/second were observed after a two-hour incubation with receptor positive cells. Strong signals can be detected after incubation for only 30 minutes. The assay can be performed in a 96-well plate using a luminometer capable of measuring this format. The signal: noise ratio was >1000 with the background subtracted and >10 without subtracting the noise in the instrument. Note that signal was easily detected within 15 minutes with a >1000-fold signal to noise ratio. This indicates that the assay can be used for high throughput drug screening.

Figure 2:
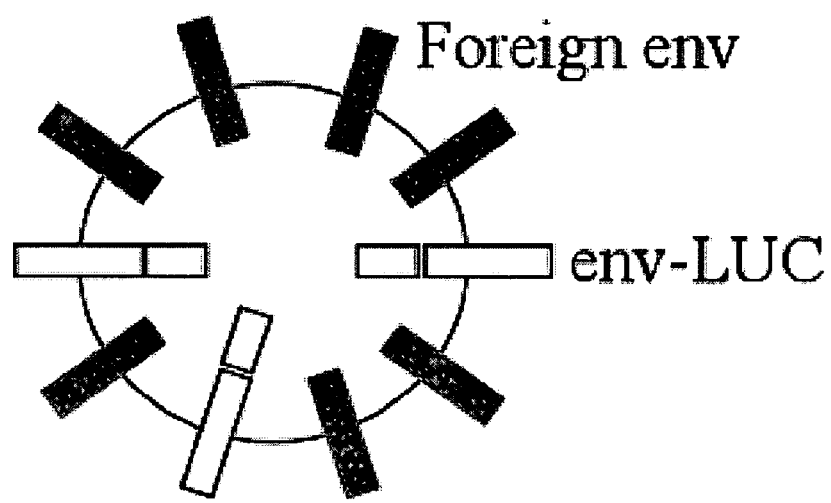
FIG. 2 shows mosaic virus containing foreign envelope proteins and envelope-luciferase construct.
Figure 3:
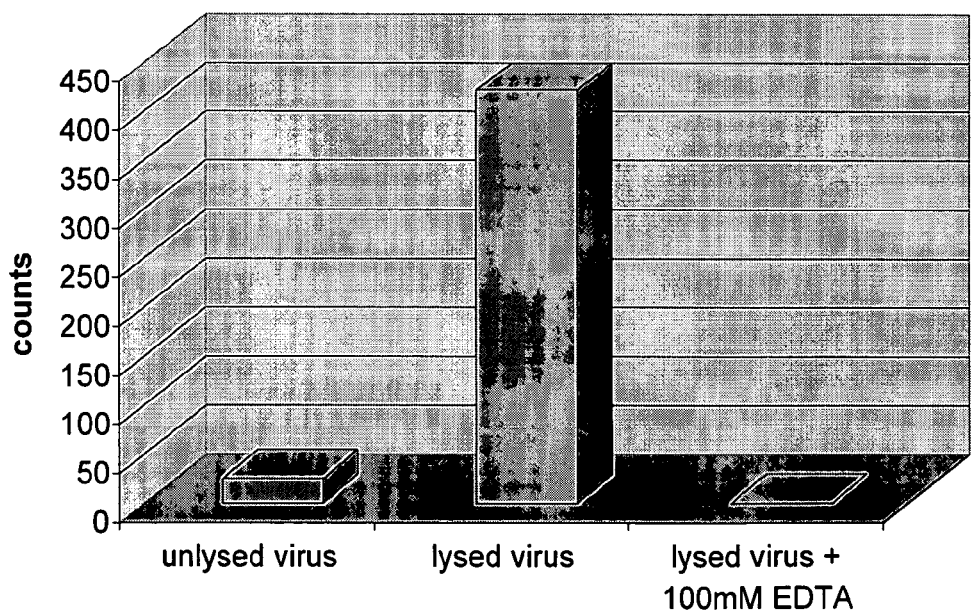
FIG. 3 shows activity of the Murine leukemia virus-Luciferase (Fr-luc) virus particles (10 ul of culture supernatant) in luciferase assay buffer. Activity increased when particles were lysed in 0.1% NP-40 detergent and was abolished by the addition of EDTA as indicated. This indicated that the luciferase was incorporated into the virus particles and likely enveloped by the viral lipid membrane. Lysis released the luciferase enzyme. EDTA chelates the $Mg^{2+}$ co-factor and inhibits the luciferase reaction.
Figure 4:
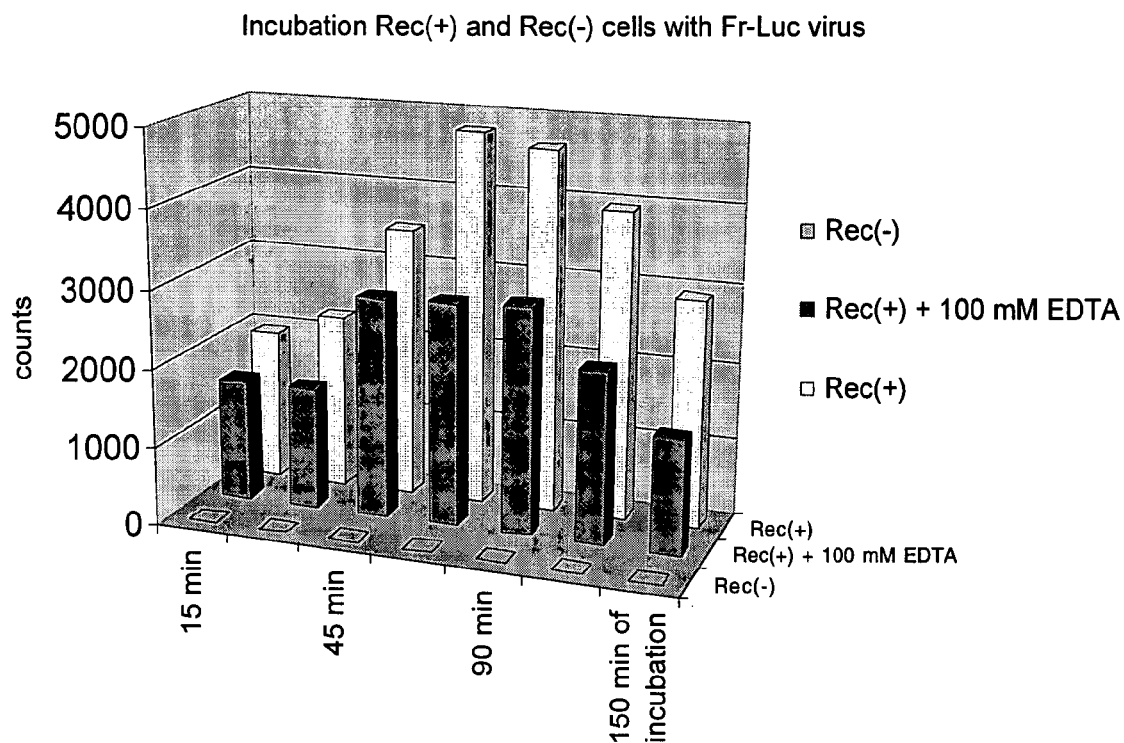
FIG. 4 shows time course of attachment and entry of the Fr-luc virus particles to cells lacking (Rec−) or bearing receptor (Rec+).
Figure 5:
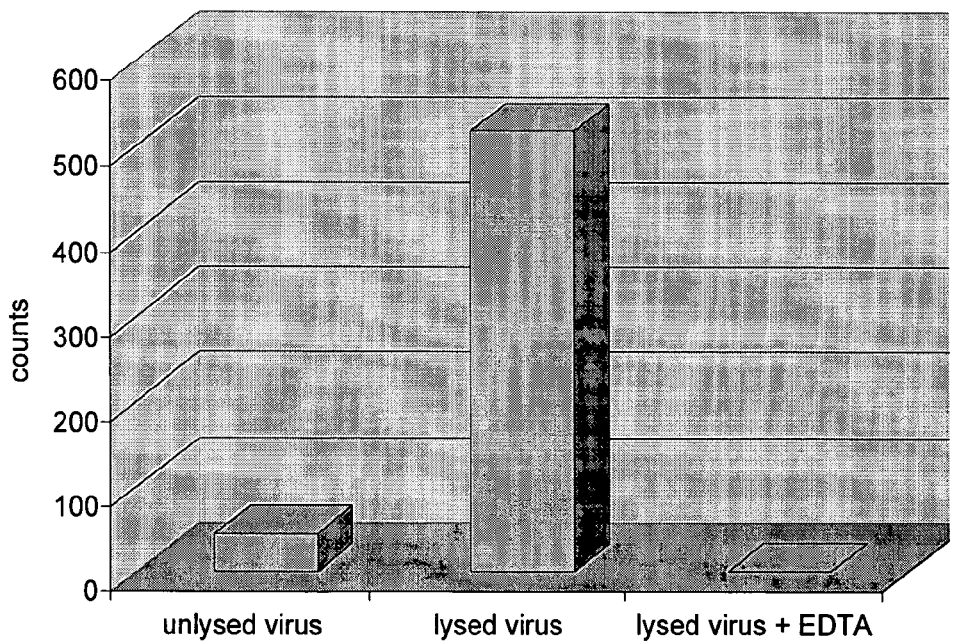
FIG. 5 shows mosaic viruses made between the VSV-G envelope and the Fr-Luc proteins by making a mixed transfection of producer cells. These particles behaved identically to the Fr-luc viruses in FIG. 1.
Figure 6:
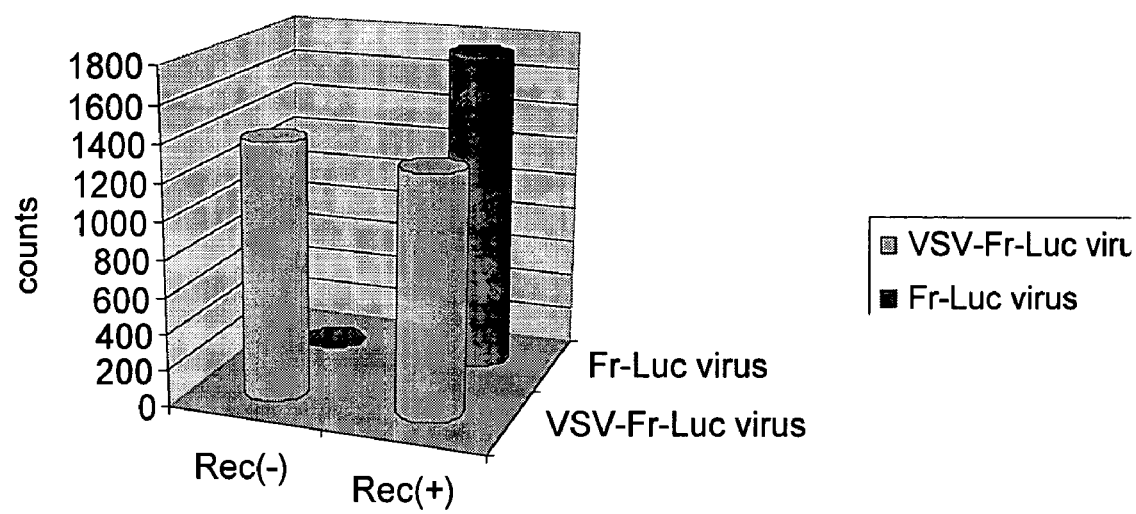
FIG. 6 shows that when applied to cells, the VSV-G+Fr-luc particles adopted the entry profile of Vesicular Stomatitis-Virus. Particles were applied to cells lacking or bearing the Fr-luc receptor but both sharing the Vesicular Stomatitis Virus receptor. Both cell types gave equal signals for the Vesicular Stomatitis Virus mosaic viruses but only that bearing the Fr-luc receptor gave a similar signal. This data demonstrates the versatility of the system in being adapted to measure cell/receptor binding and entry for other virus types without extensive modification.

Viruses expressing the murine leukemia virus (MLV) envelope proteins would enter only mouse cells or cells made to express the murine receptor by DNA transfection. Normally, human cells do not support infection. However, since the envelope-luciferase component of the virus is only one fifth of the total envelope proteins expressed on the surface, it is possible to make other MLV pseudotypes that infect human cells. Viruses that can be pseudotyped onto MLV particles include HIV (and other retroviruses), vesicular stomatitis virus (VSV), Arenaviruses (Lassa Fever agent), Hanta viruses, Ebola and Venezuelan equine encephalitis virus among others. These are natural agents of infectious disease and also potential bioterrorist agents. Therefore, this assay provides a rapid mechanism to screen for novel compounds that inhibit entry of these viruses as well. In this second embodiment, the viruses would be assembled as above, except that the wild type envelope proteins are replaced with the foreign envelope proteins of interest. The envelope-luciferase construct simply provides a mechanism to deliver the luciferase into the virus particles and should be generic. When assayed on human (or any cells other than mouse or rat) these mosaic viruses (FIG. 2) would have specificity dictated by the foreign envelope proteins. If needed the envelope-luciferase construct can be modified such that it no longer interacts with the receptor found on rat/mouse cells. This will then permit use of mouse or rat cells as well. Vesicular Stomatitis Virus-MLV mosaic viruses were made to test this approach. It was determined that the assay performed well, and it was possible to measure entry into human cells with signals similar to those described above.

Thus, the present invention is directed to a method of detecting virus binding and entry to target cells. The method steps include attaching an enzyme to the C-terminal end of a viral envelope protein, thereby creating a envelope-enzyme fusion protein; generating virus particles comprising the fusion protein and wild type viral envelope protein; infecting target cells with the virus particles; and measuring enzyme activities in the infected cells, wherein such enzyme activities are measures of virus binding and entry to the target cells mediated by the wild type viral envelope protein.

Generally, the wild type viral envelope protein is derived from viruses such as murine leukemia virus, human immunodeficiency virus, retrovirus, Vesicular Stomatitis virus, Arenaviruses, Hanta virus, Ebola virus and Venezuelan Equine Encephalitis virus. Preferably, the envelope-enzyme fusion protein comprises envelope protein of Murine leukemia virus. Examples of enzymes that can be used to generate the fusion protein include, but are not limited to, luciferase, bacterial or placental alkaline phosphatase, b-galactosidase, and fluorescent proteins such as Green fluorescent protein or toxins. The assay, in general, can also be carried out in 96-well plate.

The luciferase-based assay in the present invention was shown to measure specific adherence to cells and not non-specific breakdown of the luciferase-containing particles since only the receptor bearing cells gave signal. In addition, the present invention also demonstrated that mutant containing T471P amino acid substitution in the fusion peptide of the MLV envelope protein gave no signal but bound to cells normally. This further indicated that the assay measures only the entry of virus and not other events following virus attachment such as endocytosis or non-specific degradation of the particles that might expose the luciferase. For these experiments, binding was determined by lysing the cells and measuring total luciferase activity. This unique and highly advantageous feature of the assay that permitted the evaluation of the amino acid substitution for both virus-receptor interaction and entry in the same sample, should also permit evaluation of influence of other amino acid substitutions on entry.

The present invention is further directed to a method of evaluating amino acid substitutions on virus binding and entry. The method steps include making a mutant containing the amino acid substitution in the viral envelope protein, attaching an enzyme to the C-terminal end of mutant viral envelope protein, thereby creating a mutant envelope-enzyme fusion protein; generating virus particles comprising of the mutant fusion protein and wild type viral envelope protein; infecting target cells with the virus particles and measuring the enzyme activities in the lysed and intact infected cells, thereby enabling the evaluation of amino acid substitutions on virus binding and entry. All other aspects regarding the enzyme, envelope protein in the fusion protein, wild type envelope protein and ability of the assay to work in 96-well plate format are as described earlier.

The assay in the present invention gives an independent measure of virus entry kinetics for a retrovirus at MOI values of much less than 1. Under these conditions, signal could be detected between 5 and 20 minutes after cell contact and followed simple kinetics for over an hour. From analysis of pulse chase experiments a delay of approximately 15 minutes after virus binding to the cell occurred before significant fusion was seen. The importance of this delay remains unclear but is very similar to lags seen for HIV entry (Gallo, S. A., et.al., 2003). It may represent the time required to form a fusion pore and deliver the luciferase into the cell cytoplasm ad then access its substrates. This data is consistent with relatively slow formation of fusion pore seen for other enveloped viruses such as influenza A and VSV (Danieli, T., et.al., 1996, Paternostre, M. T., et.al., 1989). However, the lag may also indicate that cellular signaling, reorganization or trafficking events may be required for entry as suggested for HIV (Gallo et. al., 2003). These findings are consistent with a rapid mechanism of entry with similar kinetics to that seen for the pH-dependent enveloped viruses such as influenza A and VSV.

In general, enveloped viruses can be divided into those with a pH-dependent or independent mechanism of entry. The pH-dependent viruses require trafficking to acidified endosomal compartments. A block to infection by inhibitors of endosomal acidification has been used as evidence for pH dependence. However, the inhibitors used in such studies are typically cytotoxic and may affect stages of infection other than entry, such as uncoating and trafficking to cellular dNTP pool (Earp, L. J. et.al., 2003). Earlier reports had indicated that MLV have both pH-dependent (Andersen, K. B. et.al., 1983, McClure, M. O. et. al., 1990) and pH-independent (Mothes, W. et. al., 2000) mechanisms of entry.

Since the luciferase-based assay used in this invention is more rapid and quantitative measure of entry than others, it permits an extensive dissection of the virus entry pathway using inhibitors that are otherwise toxic to cells on prolonged exposure. In addition, the ability to produce VSV-G pseudotype with similar luciferase activity to that of MLV provided a control for these experiments and emphasized the flexibility of the assay system. The present invention demonstrated inhibitors of endosomal acidification inhibited signal from vesicular stomatitis virus pseudotypes but not murine leukemia virus, consistent with the pH-independent mode of entry for the later virus. It studied the effect of compounds such as chloroquine and ammonium chloride, which are weak bases that accumulate in and buffer the change in pH in endosome as well as bafilomycin A1 which is specific inhibitor on the endosomal proton pump (Mothes, W. et.al, 2000) on the viral entry. Each compound only weakly affected the signal from Friend-MLV particles. However, they inhibited the signal observed with VSV-G pseudotype, which is known to have a pH-dependent mechanism of entry. A 1000 to 10,000-fold decrease in signal was observed in signal for VSV-G pseudotype in the presence of bafilomycin and ammonium chloride, compared to at most a 2-fold change for MLV. This assay not only confirmed the previous report that MLV do not require endosomal acidification to trigger entry but also yielded a quantitative data with sensitivity that far exceeded this and other previous assays. Thus, this assay can be used to study entry mechanisms and inhibitors.

The present invention is still further directed to a method for determining whether the viral entry mechanism is dependent on pH. Assays for binding and entry are carried out as described above in the presence or absence of the inhibitors of endosomal acidification, wherein decreased enzyme activities in the presence of endosomal inhibitors indicates the virus has a pH-dependent mode of entry. All other aspects regarding the enzyme, envelope protein in the fusion protein, wild type envelope protein and ability of the assay to work in 96-well plate format are as described earlier.

Figure 7A:
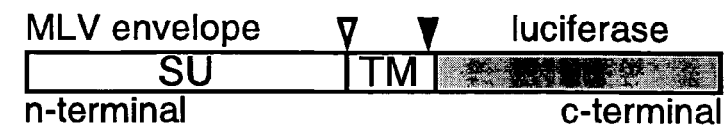
FIG. 7A shows the design of MLV envelope-luciferase fusion protein (env-luc) schematically where the open and closed arrowheads indicate native cleavage site by furin (at SU-TM junction) and viral proteases (at TM-p2e junction) respectively.

Although the methods of the present invention may be used to deliver luciferase to target cell, it can also be used to package other proteins, which can be very useful in virus-mediated therapies and nanotechnology. Based on the titration of recombinant luciferase (Quantilum, Promega) in buffer, it was possible to detect approximately 2,000 molecules. The inclusion of medium to harvest virus did not affect this number greatly. Based on the virus titer that was $10^6$ infectious particles/ml with an activity ratio of approximately $10^5$ counts/sec/ml, the specific activity was 0.1 counts/sec/infectious particle. Therefore, on the assumption that a particle/infectious-particle ratio of 10 to 100, even distribution of the enzyme and efficient lysis of virus particles, there could be between 2 to 20 molecules of luciferase packaged per particle. The present invention demonstrated that the viral particles have a finite capacity for luciferase since attempts to increase the env-luc1 protein resulted in exposure of the enzyme to the suspension buffer and loss of virus titer (FIG. 7). This was consistent with the observation that env-luc1 construct, while produced at slightly higher levels than env-luc2 in cells, incorporated poorly into particles. In comparison, env-luc2, which was incorporated well, produced particles that were permeable to luciferin. However, when the wild-type envelope and the env-luc1 construct were combined to make virus, titers were restored to normal with most virus being intact. Proteins of a similar size as luciferase (61 kDa) may also be tolerated. This design provides a simple system to package a therapeutic protein in functional virus particles, deliver it specifically to a target cell by efficient receptor-dependent targeting and have it released free of the virus into the cytoplasm of the target cell. Additionally, this is distinct from previously described methods in which genes encoding a therapeutic agent must be expressed in the target cells.

The present invention is also directed toward a method of receptor-dependent targeted therapy to an individual, comprising the steps of attaching a therapeutic protein to the C-terminal end of a viral envelope protein, thereby creating a fusion protein; generating virus particles comprising the fusion protein and wild type viral envelope protein; administering the composition to the individual, thereby enabling receptor-dependent targeted therapy to the individual. Preferably the therapeutic protein is a toxin, a chemotherapeutic agent, an immune stimulant, cytotoxic agent or attached to a radioisotope. The therapeutic protein may be about 61 kDa. All other aspects regarding the enzyme, envelope protein in the fusion protein, wild type envelope protein are as described earlier.

Additionally, the present invention is also directed to a pharmaceutical composition comprising of therapeutic protein-containing virus. All other aspects regarding the enzyme, envelope protein in the fusion protein, wild type envelope protein, the type and size of therapeutic protein are as described earlier.

Luciferase-containing virus pseudotypes may also be useful for diagnostic assays. The present invention demonstrated efficiency in the making of VSV-G chimeric virus as well as ability of the assay to work in a 96-well format without difficulty, thus enabling it to be useful in making other virus pseudotypes and also being useful for diagnostic purposes. The rapid execution of the assay would also reduce a 1-2 day diagnostic assay into several hours. This requires that the envelope protein of the donor virus and the env-luc protein accumulate on the membrane at the same locale, to be incorporated into the same particle. However, since the number of MLV pseudotypes that have been successfully produced is continually on the increase, the potential use for this assay will also expand.

The present invention is yet directed toward a method for screening neutralizing antibodies in patient sera. Assays for virus binding and entry are carried out as described earlier, where decreased enzyme activities in the patient's sera indicates that the sera has neutralizing antibodies. All other aspects regarding the enzyme, envelope protein in the fusion protein, wild type envelope protein and ability of the assay to work in 96-well plate format are as described earlier.

The present invention is also directed toward a diagnostic kit for screening neutralizing antibodies in the patients' sera, where the kit comprises (a) enzyme-containing virus pseudotypes (b) substrate for the enzyme. All other aspects regarding the enzyme, envelope protein in the fusion protein, wild type envelope protein are as described earlier. In addition, the substrate for the enzyme may be luciferin.

The present invention is further yet directed to the screening of compounds that inhibit virus binding and entry to target cells. The assays for virus binding and entry are carried out as described above in the presence or absence of the test compound, where decreased enzyme activities in the presence of the test compound indicates that the compound inhibits virus binding and entry to target cells. All other aspects regarding the enzyme, envelope protein in the fusion protein, wild type envelope protein and ability of the assay to work in 96-well plate format are as described earlier.

Luciferase containing viruses may also permit the visualization of entry events. With a sufficiently sensitive camera, it would be possible to detect the production of light upon combination of the released luciferase and substrates. Others have shown that imaging of cells expressing luciferase is possible, but requires the use of image-intensifying cameras and exposure of the sample for tens of seconds (Craig F. F. et.al., 1991). As camera sensitivity increases, this may be more practical.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

As used herein, the term "PCR" refers to the polymerase chain reaction that is subject of U.S. Pat. Nos. 4,683,195 and 4,683,202 to Mullis, as well as other improvements now known in the art.

As used herein, "restriction endonucleases" and "restriction enzymes" refer to enzymes, each of which cut double-stranded DNA at or near a specific nucleotide.

The term "oligonucleotide", as used herein, is defined as a molecule comprised of two or more ribonucleotides, preferably more than three. Its exact size will depend on many factors, which, in turn, depend upon the ultimate function and use of the oligonucleotide. The term "primer" used herein, refers to an oligonucleotide, whether occurring naturally (as in a purified restriction digest) or produced synthetically, and which is capable of initiating synthesis of a strand complementary to a nucleic acid when placed under appropriate conditions, i.e., in the presence of nucleotides and an inducing agent, such as a DNA polymerase, and at a suitable temperature and pH. The primer may either be single-stranded or double-stranded and must be sufficiently long to prime the synthesis of the desired extension product in the presence of inducing agent. The exact length of the primer will depend upon many factors, including temperature, sequence and/or homology of primer and the method used. For example, in diagnostic applications, the oligonucleotide primer typically contains 15-25 or more nucleotides, depending upon the complexity of the target sequence, although it may contain fewer nucleotides.

The primers used herein are selected to be "substantially" complementary to particular target DNA sequences. This means that the primers must be sufficiently complementary to hybridize with their respective strands. Therefore, the primer sequence need not reflect the exact sequence of the template. For example, a non-complementary nucleotide fragment (i.e., containing a restriction site) may be attached to the 5' end of the primer, with the remainder of the primer sequence being complementary to the strand. Alternatively, non-complementary bases or longer sequences can be interspersed into the primer, provided that the primer sequence has sufficient complementary bases with the sequence to hybridize therewith and form the template for synthesis of the extension product.

It is also contemplated that pharmaceutical compositions may be prepared using the therapeutic protein-containing virus pseudotypes of the present invention. In such a case, the pharmaceutical composition comprises the novel active composition of the present invention and a pharmaceutically acceptable carrier. A person having ordinary skill in this art would readily be able to determine, without undue experimentation, the appropriate dosages and routes of administration of the active component of the present invention.

The phrase "pharmaceutically acceptable" refers to molecular entities and compositions that do not produce an allergic or similar untoward reaction when administered to a subject. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A protein may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids such as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media, which can be employed, will be known to those of skill in the art in light of present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15$^{th}$ Edition, pages 1035-1038 and 1570-1580). Some variation in dosage will necessarily occur depending on the condition of the subject being treated. The person responsible for administration will, in any event, determine the appropriate dose for the individual subject.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Construction of Envelope-Luciferase Construct

The envelope-luciferase fusion vector was made by modifying the 3' end of the Friend 57 Murine Leukemia Virus envelope protein to replace the native stop codon with an EcoRV restriction endonuclease site. This was achieved using PCR. Primers used: 5' CCATCGATTAGT-TCAATTTGTTAAAGACAG 3' (SEQ ID No 1) and 5' GATCGAATTCTGGCTCGTATTCTAGTGGTTTTAGC 3' (SEQ ID No 2). The firefly luciferase gene was modified to gain an EcoRV restriction endonuclease site at its 5' end. A short linking peptide (Serine-Glycine) was also added in the same reaction. The primers used: 5' GATCGAATTCGAA-GACGCCAAAAACATAAAGAAAG 3' (SEQ ID No 3) and 5' GATGCGGCCGCTTACACGGCGATCTTTC-CGCCCTT 3' (SEQ ID No 4). The latter primer also gave two tandem stop codons followed by a NotI restriction endonuclease site at the 3' end of the gene. The recombinant MLV envelope gene was then cloned into a standard expression vector (pCDNA3) using a native HindIII site at its 5' end and the artificial EcoRV site. The modified luciferase gene was then added using sites EcoRV and NotI. The construct was sequenced and had the predicted nucleotide sequence.

The construct was tested by producing MLV pseudotyped viruses bearing the envelope-luciferase fusion protein. To do this cells were simultaneously transfected with plasmids encoding 1) the envelope-luciferase fusion protein, 2) the MLV polymerase, capsid and matrix proteins (gag-pol gene) and 3) a packageable marker gene such as b-galactosoidase or jellyfish green fluourescent protein (permits determination of virus titer by conventional gene expression methods). Transfection was by standard calcium phosphate mediated transfection methods. After two days the supernatant was collected and filtered through a 0.45 mm cellulose acetate filter and either used immediately or frozen at −80° C. To perform an entry assay, fresh cells ($10^4$-$10^5$) were incubated with 0.2-1.0 ml of virus containing culture supernatant for times up to 2 hours. Cells were then collected by 1 min centrifugation at 1000 xg and the supernatant was aspirated off.

It has been previously shown that intact cells can be efficiently perfused with luciferin (the luciferase substrate). This provides a simple and rapid way to measure if virus has fused to the cell membrane by measuring release of the encapsidated luciferase enzyme into the luciferin and ATP (substrates of luciferase) containing cytoplasm of the cell. Therefore, isotonic luciferase buffer (modified from Promega by addition of sodium acetate to 50 mM) was added.

To ascertain the amount of virus that had penetrated the cell versus that bound on the surface, cells were either incubated intact (shows how much virus entered the cell by fusion with the cell membrane) in this buffer or lysed (total=entered+bound on surface) in 0.1% NP-40 detergent. Measurements were made using a standard luminometer after 5 minutes but could be performed sooner without much change in the signal.

As the entry assay relies on the encapsidation of the marker enzyme (luciferase) within the luciferin impermeable viral membrane it was necessary to optimize conditions to achieve this. The amount of plasmid encoding the native envelope protein was adjusted from 0 to 5 mg and sufficient envelope-luciferase encoding plasmid was added to give a total of 5 mg in the transfection mixture. It was found that 5 times more native envelope protein was optimal for virus particle production, maximal luciferase activity in detergent lysed virus and minimal activity in unlysed particles. This indicated that under these conditions the luciferase protein is efficiently encapsidated in intact virions. Reducing the amount of native envelope encoding plasmid resulted in particles that gave lower virus titer. They also gave luciferase activity without lysis. This indicated that the particles were defective, with breaches in the viral envelope membrane and were not suitable for use in this assay.

To perform the assay in 96 well format, $10^4$ cells were seeded into each well and 0.2 ml of virus containing culture supernatant was incubated with the cells for 1 hour. After this time the supernatant was removed and luciferase buffer (as above) was added with or without detergent. The plates were then analyzed in a standard luminescent plate reader.

Assays were also performed without removal of the culture supernatant by addition of the luciferase buffer directly to the mixture. In this case the signal was approximately 80% that obtained when the culture medium was completely replaced.

EXAMPLE 2

Construction of Envelope-Luciferase 1 (env-luc1) and Envelope-luciferase 2 (env-luc2) Constructs:

It is known that the envelope protein of the murine leukemia virus (MLV) is made as a single polypeptide that is cleaved in the endoplasmic reticulum into two subunits, SU (70 kDa) and TM (15 kDa). TM that anchors the complex to the cell and eventually to virus membranes is cleaved by a viral protease to release a C-terminal peptide, p2e immediately before or just after budding from cell. This has been shown to be important for infection competency of the virus (Rein, et al., 1994). Therefore, fusion of proteins to the C-terminus of TM would provide a novel method of delivering recombinant protein to the viral lumen, between the membrane and matrix shell of the viral core. The cleavage of the protein by viral protease after budding would also release the luciferase permitting it to diffuse into the cell cytoplasm after membrane fusion.

To test this, two constructs, env-luc1 and env-luc2 differing in the length of the spacer peptide that fused the Friends57 MLV envelope to the N-terminus of the luciferase gene (FIG. 7A) were made. The env-luc fusion vector was made by modifying the 3' end of the Friend57 murine leukemia virus (MLV) envelope gene to replace native stop codon with an EcoRI restriction endonuclease site. This was achieved by performing PCR using primers of SEQ ID Nos. 1 and 2. The firefly luciferase gene was modified to gain an EcoRI restriction endonuclease site at its 5' end. A short linking peptide (Glu-phe) and (Glu-Phe-Gly-Ser, SEQ ID No 5) for env-luc1 and env-luc2 respectively was added in the same reaction through the EcoRI site. The primers of SEQ ID Nos. 3 and 4 were used for this. The later primer also gave two tandem stop codons, followed by a NotI restriction endonuclease site at the 3' end of the gene. The recombinant MLV envelope gene was then cloned into pCDNA3 (Invitrogen) using a native HindIII site at its 5' end and the artificial EcoRI site. The modified luciferase gene was then added using EcoRI and NotI sites. The constructs were sequenced and had the predicted nucleotide sequence.

The MLV viruses were made with env-luc1 and env-luc2 constructs and pψ-EGFP plasmid substituted pFB-luciferase vector, thereby permitting direct determination of virus titer by infecting cells and counting colonies expressing EGFP.

In general, the production of pseudotyped MLV and viruses containing envelope-luciferase fusion protein can be explained briefly as follows: 293 HEK cells grown to 80% confluence were transfected by calcium phosphate method (Chen and Okayama, 1987). 5 µg of each plasmid was used: 1. pGAG-POL (encoding the MLV gag and polymerase), 2. pEnv (Friend57 envelope protein in pcDNA3) or pVSV-G (G protein of vesicular stomatitis virus), 3. pψ β-gal or pψ EGFP (encode β-galactosidase or enhanced green fluorescent protein, Clontech, respectively, under control of the MLVLTR and packaging sequence). To make virus containing the env-luc1 fusion protein, 1 µg of this construct was added to the mixture unless stated otherwise. After overnight incubation, the medium was replaced with fresh medium and incubated for a total of 36 hours. The supernatants were then collected and filtered through a 0.45 µm cellulose acetate filter. The filtrate was then used either directly or the virus is pelleted by 1 h centrifugation at 16,000 xg and the pellet used. In some experiments, virus was collected by pelleting through cushion of 20% (w/v) sucrose, 10 mM Tris-Hcl, pH 7.4.

Luciferase was present in the supernatent for both the constructs. Most of this activity was also pelleted by centrifugation and penetrated a 20% sucrose cushion at 20,000 xg, a characteristic of intact MLV particles. The pelleted material was also associated with infectious virus and gave the titers of $3 \times 10^3$ and $4 \times 10^4$ cfu/ml for env-luc1 and env-luc2, respectively. In later experiments, sucrose gradients (5-60% were also used to purify the virus. It was observed that >90% of the luciferase activity comigrated with the infectious virus peak.

Figure 7B:
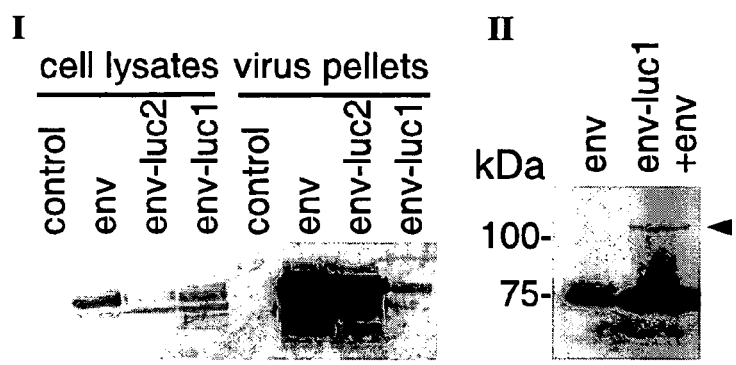
FIG. 7B shows the western blots of lysates from cells transfected with plasmids encoding wild-type Friend MLV envelope (env) alone or with env-luc1 and env-luc2 constructs or expression vector pCDNA3 (control) alone and pelleted particles collected from the culture supernatants. Blots containing cells lysed in 1% NP-40 were probed with anti-Rauscher MLV (anti-env) antibody that cross-reacts with Friend MLV envelope protein.

Western blots probed with anti-SU showed differences in the levels of production of each construct in the cells and incorporation in particles (FIG. 7B (I)). Each was processed rapidly to the native SU band. The env-luc1 protein was produced at similar levels to wild type envelope protein, while lower amounts of env-luc2 were detected. However, env-luc2 was incorporated more efficiently in particles than env-luc1. By increasing the amount of plasmid encoding wild type envelope protein in the transfection mixture, an uncleaved precursor for env-luc1 was observed in cell lysates migrating above 100 kDa (FIG. 7B (II), right panel), this band was absent in the pelleted material. This indicated that the env-luc protein was processed correctly by cellular proteases into SU and TM. Although attempts to detect luciferase-TM product on Western blots were unsuccessful due to lack of a sensitive anti-luciferase antibodies (data not shown), the fact that luciferase was present in the infection mixture indicated that enzyme had been successfully incorporated.

To measure entry, the luciferase would have to be encapsidated in intact virions impermeable to the luciferase substrates. The luciferase activity was measured in the presence or absence of 1% NP-40, which permeabilize MLV that are normally impermeable to small solutes such as dNTPs (Mothes, W., et.al, 2000). It was observed that virus made with env-luc1 gave a 3-fold higher luciferase activity than the virus made with env-luc2. However, it was observed that addition of NP-40 increased the signal for both env-luc1 and env-luc2. The ratio of luciferase activity for lysed versus unlysed virus for env-luc1 was 15 and for env-luc2 was 1. This indicated that although both the constructs successfully targeted luciferase into the virus, incorporation of env-luc2 was more disruptive, resulting in a greater number of membrane breaches compared to most virus made with env-luc1, which were intact (Table 1). This also indicated that the particles have a finite capacity for luciferase and that env-luc1 limits this by being poorly incorporated.

(w/v) sucrose cushion and pelleted material was collected after 1 h at 16,000 xg. Cells and pellets were lysed by resuspension in 1.0 ml or 0.1 ml of 1% NP-40, respectively. 10 μl was then used to determine the luciferase activity. Ratio equals to luciferase activity in lysed to unlysed cells. N.d.=not determined.

Figure 7C:
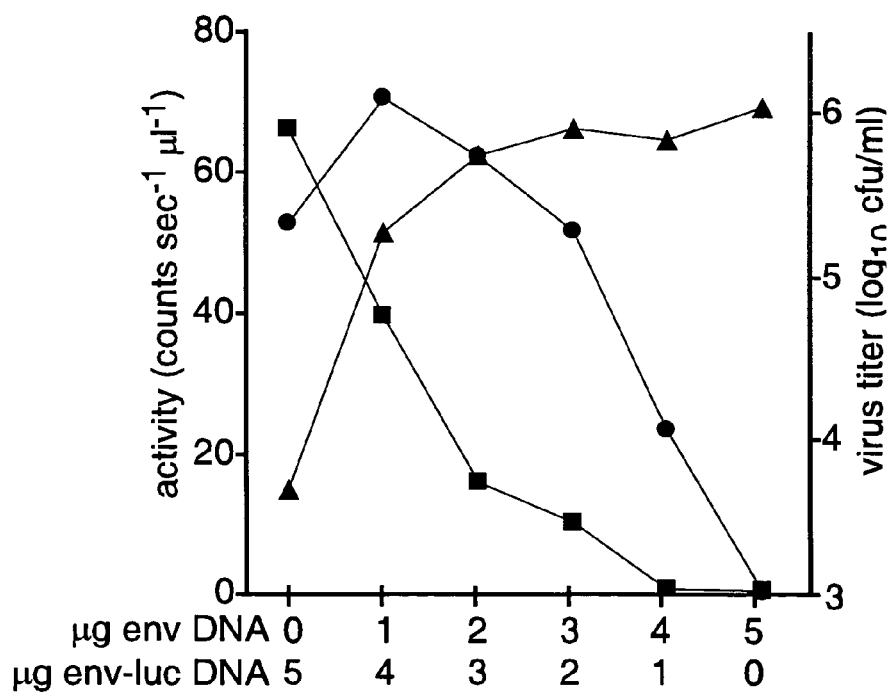
FIG. 7C shows optimization of virus production by varying the ratio of env-luc1 to wild type envelope protein and determining the luciferase activity (left axis) for intact (squares) and lysed (circles, 1% NP-40) particles. Virus titer (triangles, right axis) was determined by infecting 293-CAT cells in serial, five-fold dilutions and staining them for β-galactosidase after 2 days.

In order to optimize the virus production, the titer of virus made with env-luc1 was raised ($10^3$ cfu/ml compared to $10^6$ cfu/ml for wild type virus) by addition of wild type envelope encoding plasmid in the transfection mixture. The ratio of env-luc1 to wild type envelope encoding plasmid was adjusted and the lysed:unlysed luciferase signal ratio and virus titer were measured by marker gene expression (FIG. 7C). It was observed that a ratio of 4:1 env-luc1 to wild type envelope plasmid, gave a virus of low titer and high lysed:unlysed signal ratio compared to ratio of 1:4, which improved the virus titer to $1 \times 10^6$ cfu/ml, similar to wild type envelope plasmid alone and a lysed:unlysed signal ratio of 10:1. Over a series of six separate experiments, the average ratio was 11.2+/−3.7. Thus, together these data indicated that these virus particles should act as a molecular beacon, with signal being produced after the luciferase is released by fusion of cell and virus membrane and a signal to noise ratio of at least 10-fold.

In order to determine if these particles would produce a receptor-dependent entry signal, these particles were incubated with 293 cells bearing receptor (293-CAT) or lacking receptor (293). 293 cells are not permissive for ecotropic MLV infection until they are made to express mCAT-1, the ecotropic MLV receptor and hence, these served as a negative control. A clone of 293 cells expressing recombinant mCAT-1 with a c-terminal HA-tag, termed 293-CAT was used as a target (Davey et al., 1999).

In general, the entry assay was performed by incubating cells (typically $10^5$/sample) for 1 h with env-luc1 containing virus at an MOI of 0.1-0.5. Excess virus was washed free of cells by pelleting by centrifugation at 200 xg for 5 min and resuspending in DMEM. The cells were pelleted again and resuspended in 0.1 ml of luciferase assay buffer (Promega). Luciferase activity was measured after 1 min in a Turner Designs TD 20/20 luminometer and expressed as counts/sec. The assay was also performed in a 96-well plate using $10^4$ cells per well. While the signal was reduced proportionally, it remained at least 10-fold above the background of the detector (Perkin-Elmer plate reader).

In this case, cells were incubated in the presence of 0.5 ml of virus containing culture medium for times up to 2 h at 37°

TABLE 1

Encapsidation of luciferase into virus particles

| Plasmids transfected | | | | | | Luciferase activity (counts/sec/10 μl) | | | |
|---|---|---|---|---|---|---|---|---|---|
| PFB-ψluc | PψEGFP | pGag-pol | pEnv | pEnv-luc1 | pEnv-luc2 | Cell lysate | supernatant | pellet | Ratio |
| − | + | + | + | − | − | 0 | 10 | 8 | n.d. |
| + | − | + | + | − | − | 574,000 | 1,101 | 22 | n.d. |
| − | + | + | − | + | − | 2,212,000 | 556 | 975 | 15 |
| − | + | + | − | − | + | 2,022,000 | 350 | 243 | 1 |
| − | + | + | + | + | − | n.d. | 2,145 | 2,891 | 11 |

293 cells transfected with the plasmids as indicated and the luciferase activity in the supernatants was tested after harvesting (36 h after transfection) and filtering (0.45 μm). Part of the supernatant (0.25 ml) was overlayed on a 0.5 ml 20%

Figure 8:
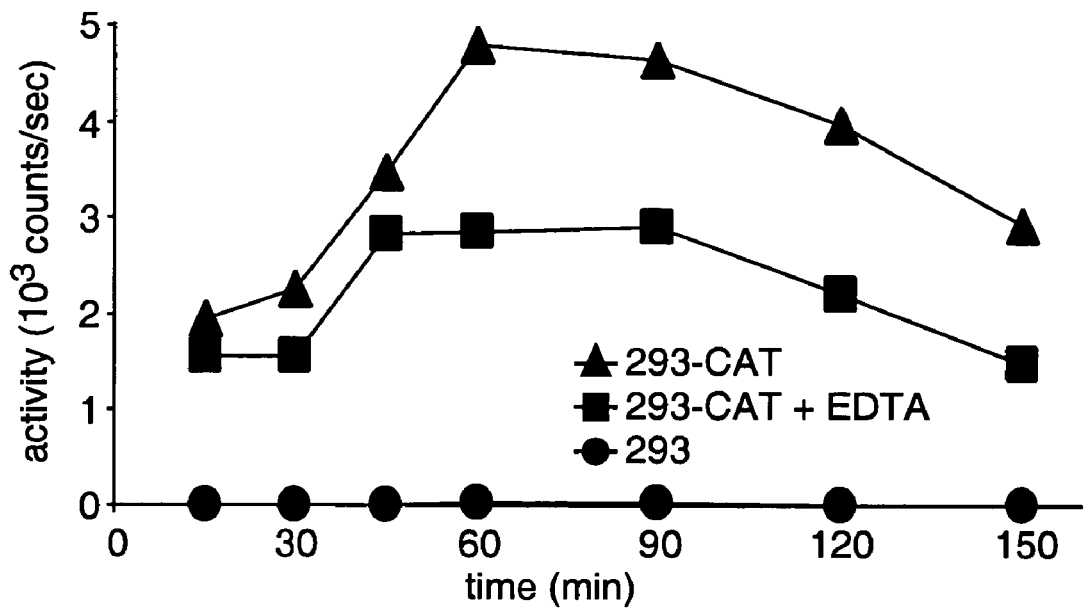
FIG. 8 shows luciferase activity of virus mixture incubated over time with 293 cells bearing receptor (293-CAT, triangles) and not when incubated with 293 cells lacking receptors (293, circles) in intact cells. It also shows the amount of luciferase that was exposed on the cell surface by adding EDTA (100 mM, squares) immediately before the addition of the luciferase substrates.

C. with gentle mixing. Cells were then pelleted, washed free of unbound virus and assayed for luciferase activity by incubating the cells directly in luciferase buffer. Signals were detected on cells bearing virus receptor. The signals peaked 1 minute after addition of the assay buffer, which was consistent with rapid uptake and equilibration of luciferin into the cells (FIG. 8, triangles). Similar kinetics was observed with cells transfected with a luciferase-encoding plasmid (pFB-luc, data not shown). Cells expressing the receptor gave a signal that peaked after 1-1.5 h at 5000 counts/sec (FIG. 8, triangles). No activity above the background signal of the luminometer (approx. 10 counts/sec) was observed for 293 cells. In other experiments, it was observed that the magnitude of the signal changed in direct proportion to the number of receptor-bearing cells ($10^4$-$10^7$) or amount of virus used (MOI of 0.01-10, data not shown). These observations demonstrated that particles containing luciferase were successfully targeted to receptor bearing cells, which produced a signal that was consistent with receptor-dependent exposure of the enzyme.

In order to determine the portion of the signal from virus having entered the cell from that of particles that had broken open on the cell surface, suspension or residual defective particles, 100 mM EDTA (isotonic), pH 7.4 was added to the sample. Since luciferase requires MgATP to function, this treatment effectively inhibits activity by sequestering the $Mg^{2+}$ present in the supernatent. It was observed that the signal dropped on average, by 30% with the remainder being resistant (FIG. 8, squares). In other experiments, EDTA inhibited the activity to 10-20%. These observations were consistent with the virus-associated luciferase being taken into an EDTA-inaccessible compartment by either receptor-dependent endocytosis or fusion of the virus membrane with cell membranes. The EDTA-sensitive portion may be due to the residual permeable, defective particles bound to cells or virus in early stages of entry that may be more easily disrupted.

Figures 9A, 9B:
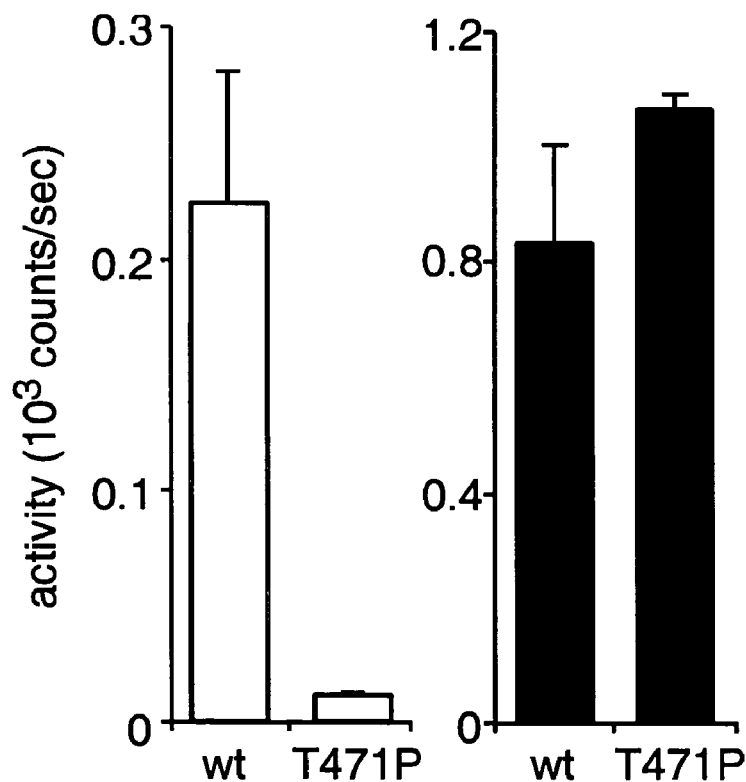
FIG. 9 (9A and 9B) shows the measurement of luciferase activity for analysis of fusion peptide point mutation, T471P using the entry assay. A single amino acid substitution, T471P was made in the Friend MLV envelope protein and in the env-luc1 construct. Virus was produced, lysed in 1% NP40 and matched to luciferase activity of virus-bearing wild-type envelope protein and env-luc1. This was applied to cells and the luciferase activity was measured after 1 hour on intact cells (FIG. 9A, left panel) or in the presence of 1% NP40 (FIG. 9B, right panel).

Introduction of a Single Amino Acid Substitution, T471P, in Friend MLV Envelope Protein and in the env-luc1 Construct To further confirm that the signal measured was due to penetration of the virus-associated luciferase into cells through virus mediated membrane fusion, a point mutation, T471P was introduced in the envelope protein. This change was previously characterized and shown to bind cells but not infect them (Zhu, N. L., et.al., 1998). The fusion peptide mutant was made by PCR mediated site directed mutagenesis as described earlier (Zhu, N. L., et.al., 1998). The sense strand oligonucleotide for the T471P mutation was 5' CGC-CGCGGGAGTTAGGGCCCGGAACTACCGCC 3' (SEQ ID No 6), which added an ApaI endonuclease site (underlined). The fragment of DNA encoding the changes was cloned into native KpnI and ClaI sites in the Friend57 ecotropic envelope gene and into env-luc1 construct. Base changes were confirmed by restriction enzyme cleavage using ApaI and sequencing. The mutation was placed in both the Friend MLV envelope protein and the env-luc1 construct. Virus was produced and cells were challenged. The supernatent containing virus with the T471P mutation gave a similar luciferase activity to that of the wild type of 40 counts/sec/µl and a typical lysed:unlysed ratio of at least 5. After 1 hour of incubation, the T471P mutant gave a signal that was close to the background signal of the luminometer and 20-fold lower than that for wild type virus (FIG. 9A, left panel). Addition of 1% NP-40 detergent to expose the encapsidated luciferase and permit determination of total cell-associated activity, gave similar activities for both wild type and the T471P mutant (FIG. 9B, right panel). In a separate experiment, little activity was present in 293 cell lysates. This indicated that the T471P mutant virus had bound to cells normally but had not exposed the encapsidated luciferase. Together these data strongly support the conclusion that the assay is measuring receptor-mediated fusion of virus to cells and delivery of the luciferase enzyme in cell cytoplasm.

Production of MLV Pseudotype Bearing the Envelope Protein of Vesicular Stomatitis Virus with env-luc1

To demonstrate that the luciferase could measure inhibition of entry for a pH-dependent virus, an MLV pseudotype bearing the envelope protein of vesicular stomatitis virus (VSV-G) together with env-luc1 was constructed. The VSV pseudotypes of MLV have been previously reported and enter cells through a VSV-G dependent mechanism (Burns, J. C. et.al., 1993, Que, X. et.al., 1999) possibly by clathrin-mediated endocytosis. VSV have also been shown to a have a pH-dependent fusion mechanism in vitro (Blumenthal. R., et.al. 1987, Paternostre, M. T., et.al., 1989). Since the env-luc1 protein would not participate in entry if assays were performed on 293 cells lacking the ecotropic receptor as shown by data in FIG. 8, a VSV-G/env-luc1 chimeric virus was made by substituting the Friend envelope expression plasmid with that of VSV-G as stated earlier. The VSV-G/env-luc chimeric virus was collected and gave a lysed:unlysed ratio of 8.7+/−2.2, which was slightly lower than the original Friend envelope containing virus but still demonstrating that most of the particles encapsidated luciferase. The overall activity of the lysed particles was one-half of the Friend virus, being 10 counts/sec/µl of culture supernatent.

The activity of three inhibitors of endosomal acidification on the VSV-G and Friend MLV luciferase-containing viruses was then tested. In general, the cells were treated with the lysosomotropic agents as follows: Chloroquine, bafilomycin A1 and ammonium chloride were the three inhibitors that were used in this experiment. Ammonium chloride and chloroquine were dissolved directly in DMEM and incubated with cells for 1 h before and during incubation with virus. Bafilomycin A1 was first dissolved in DMSO as a 50 µM stock and diluted in DMEM before use. Each of the three drugs were compared by measuring the effect on the infection efficiency, as measured by staining in a conventional reporter gene expression assay, after 2 days or in the luciferase entry assay after 1 hour incubation (FIG. 10). In this experiment, the number of cells ($10^6$) and the virus used per sample were increased by 10-fold. This gave a proportional increase in signal and sensitivity.

The β-galactosidase infection assay that measured the reporter enzyme expression after 36 hours showed that infection of VSV-G pseudotype was more sensitive to each drug, with bafilomycin being the most potent, reducing infection by 100-fold at 4 nM (FIG. 10A, solid bars). The luciferase assay, by comparison was more sensitive for the VSV-G pseudotypes. It was observed that 2 mM and 40 nM of ammonium chloride and bafilomycin respectively, decreased the signal by 1000 to 10,000-fold (FIG. 10B, right panel, solid bars). Chloroquine, which was not as effective, inhibited the infection and the entry signal by only 20 and 7-fold respectively. When the Friend pseudotype was used, the infection was inhibited weakly by all of the drugs up to 3-fold which, represents a relatively small decrease in virus titer from $10^6$ to $3\times10^5$ cfu/ml. Similarly the luciferase activity for this virus was decreased by no more than 2-fold (FIG. 10B, open bars). In comparison to VSV-G pseudotype, this change is small and reflects slight cytotoxic effects of each drug on the cells.

To check that the drugs did not alter the permeability of cells to luciferin and access to ATP, cells were infected with a luciferase expressing retrovirus made using the plasmid, pFB-ψluc (Stratagene) and luciferase activity was measured two days later. At the concentrations used, little change in the signal was observed after the cells were incubated in luciferase buffer.

In addition the cells were incubated with luciferase containing Friend and VSV-G pseudotyped virus and the drug was then added after 1 hour and luciferase activity measured. When assayed for activity, the cells showed similar small changes in signal compared to cells pre-incubated with drug. Thus, the assay measured the entry of virus and confirmed that the inhibitors of endosomal acidification did not significantly affect the entry of ecotropic MLV.

Figure 11:
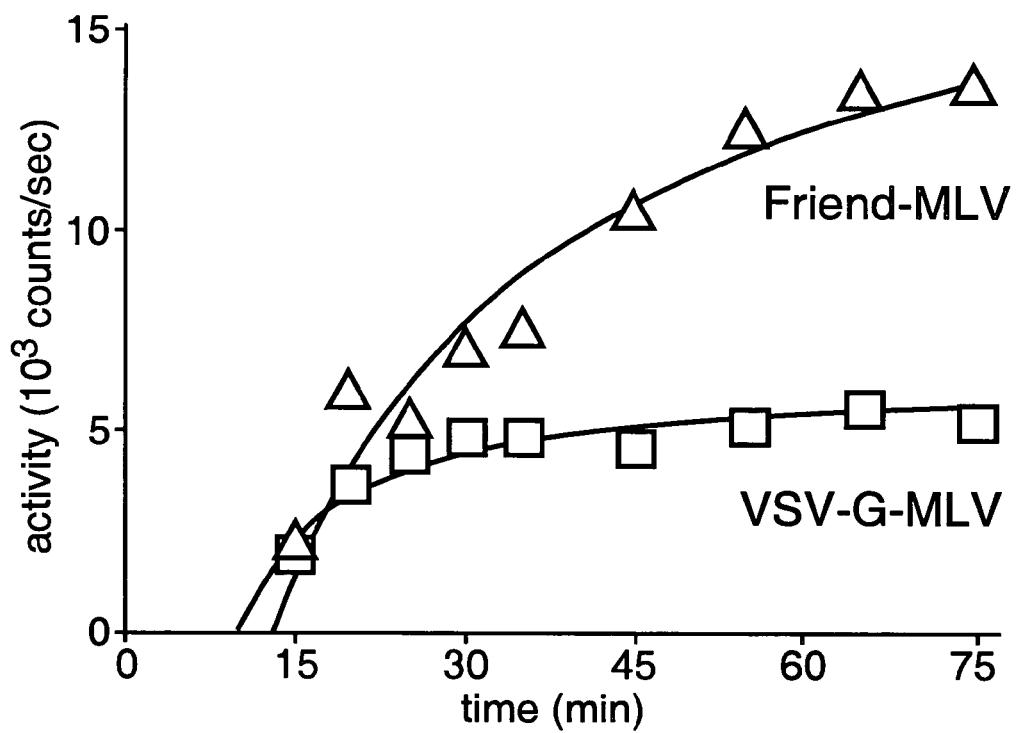
FIG. 11 shows pulse chase analysis of entry kinetics using the luciferase assay. Cells ($2 \times 10^6$) were incubated with luciferase containing Friend-MLV (triangles) or VSV-G MLV (squares) pseudotyped virus at an MOI of 0.5 for 5 minutes at 37° C. Samples were then collected at the times indicated (calculated from the time of virus addition) and activity was measured as described previously. Curves (rectangular hyperbola) were fitted to data by non-linear regression analysis using GraphPad Prism version 4.00 for Windows, (GraphPad Software, San Diego, Calif., USA).

Since the kinetics of entry for MLV was poorly understood, pulse-labeling experiment was performed, using the luciferase assay to measure the virus entry of Friend MLV and VSV-G pseudotypes. The particles were incubated with 293 or 293-CAT cells for 5 minutes and unbound virus were removed by rapid washing. Cells were then incubated at 37° C. with gentle agitation and the luciferase activity was measured at different time points for up to 75 minutes (FIG. 11). For both the pseudotypes, the earliest time point at which the luciferase activity was detectable was 10 minutes after the excess virus had been removed by washing. For the Friend MLV, this signal grew steadily and began to plateau at 75 minutes (FIG. 11). A non-linear regression analysis showed that half of the particles had fused with cells by 40+/−1.3 minutes post binding ($R^2=0.94$). For the VSV-G MLV pseudotype, it was observed that the kinetics was more rapid, reaching a plateau at 30 minutes (FIG. 11). A similar linear regression analysis showed that the half of signal was reached by 18+/−1.2 minutes ($R^2=0.87$). The signal obtained from the VSV MLV was approximately 3-fold lower than that for Friend MLV.

To test if this difference was due to lower amounts of VSV MLV virus being bound to cells and to ensure that similar amounts of virus had remained bound to cells during the chase phase of the experiment, $^{35}$S-methionine labeled, density gradient purified virus was included in the assay. The $^{35}$S-methionine labeled virus were produced as follows. One day after transfection with plasmids, cells were washed twice in DMEM, and then incubated overnight in methionine-free DMEM, containing 0.25 mCi of cell labeling grade $^{35}$S-methionine (Amersham). Virus containing supernatants were collected, filtered and particles were pelleted through a 20% sucrose cushion by centrifugation at 20,000 xg for 3 hours. The pellet was collected in PBS and used. To ensure that radioactivity was associated with the virus particles, some of the supernatant was applied to a Sepharose CL-4B column (Sigma) and the amount eluting with the void volume and retained volumes was measured by scintillation counting. 80-90% radioactivity was observed in the void for VSV and Friend MLV, indicating that it was most likely associated with the virus particles and was not free methionine. Cells were then incubated for 5 minutes with virus and rapidly washed three times, by gentle pelleting at 200 xg for 3 min and resuspension in DMEM. They were then incubated at 37° C. with gentle agitation and used for measurements at the times given.

Over the entire time course, the cell associated virus remained relatively constant with an average of 4.3+/−0.4% of the input VSV-G containing particles being bound to cells, corresponding to a final MOI of 0.002 (titer of virus on 293-CAT cells was $1.3 \times 10^6$ cfu/ml). For the Friend MLV 10.4+/−1% of the input virus was cell associated, corresponding to MOI of 0.006 (titer was $1.5 \times 10^6$ cfu/ml). These results indicated that the observed difference in the VSV-MLV and Friend MLV plateaus was due to the amount of virus that had bound during the 5 min pre-incubation and that a similar proportion of each was able to yield a signal. In other experiments, with extended time courses, it was observed that by 2.5 hours, the signal had dropped to 60% of the peak at 75 min, similar to FIG. 8. This indicated that the signal was labile with a half-life of >2.5 h. However, this slow decay should have little effect on this analysis.

The following references were cited herein:

Blumenthal, et al., (published erratum appears in *J Biol Chem* 263(1):588, Jan. 5, 1988) *J Biol Chem* 262:13614-9, 1987.
Danieli, et al., *J Cell Biol* 133:559-69, 1996.
Erlwein, et al., *J Gen Virol* 84:369-73, 2003.
McDonald, et al., *J Cell Biol* 159:441-52, 2002.
Spitzer, et al., *J Virol* 77:6070-5, 2003.
Edinger, et al., *Virology* 249:367-78, 1998.
Sharron, et al., *Blood* 96:41-9, 2000.
Cavrois, et al., *Nat Biotechnol* 20:1151-4, 2002.
Gallo, et al., *Biochim Biophys Acta* 1614:36-50, 2003.
Paternostre, et al., *FEBS Lett* 243:251-8, 1989.
Earp, et al., *J Virol* 77:3058-66, 2003.
Andersen, et al., *Virology* 125:85-98, 1983.
McClure, et al., *J Gen Virol* 71 (Pt 4):767-773, 1990.
Mothes, et al., *Cell* 103:679-89, 2000.
Rein, et al., *J Virol* 68:1773-81, 1994.
Chen, et al., *Mol Cell Biol* 7:2745-52, 1987.
Davey, et al., *J Virol* 73:3758-63, 1999.
Zhu, et al., *J Virol* 72:1632-9, 1998.
Burns, et al., *Proc Natl Acad Sci USA* 90:8033-7, 1993.
Que, et al., *Mol Biochem Parasitol* 99:237-45, 1999.
Craig, et.al., *Biochem J* 276 (Pt 3):637-41, 1991.

What is claimed is:

1. A method of screening for a compound that inhibits virus binding and entry to target cell mediated by a wild type viral envelope protein, said method comprises the steps of:
    attaching an enzyme to the C-terminal end of a viral envelope protein, thereby creating an envelope-enzyme fusion protein;
    generating virus particles comprising said fusion protein and the wild type viral envelope protein, wherein the enzyme of the envelope-enzyme fusion protein is encapsulated into the virus particles;
    infecting target cells with said virus particles in the presence or absence of said compound; and
    measuring activities of said enzyme in said infected cells, wherein decreased enzyme activities in the presence of said compound indicates that said compound inhibits virus binding and entry to said target cells mediated by said wild type viral envelope protein.

2. The method of claim 1, wherein said enzyme is luciferase.

3. The method of claim 1, wherein said envelope-enzyme fusion protein comprises envelope protein of murine leukemia virus.

4. The method of claim 1, wherein said wild type viral envelope protein is from a virus selected from the group consisting of murine leukemia virus, human immunodeficiency virus, retrovirus, Vesicular Stomatitis virus, Arenaviruses, Hanta virus, Ebola virus and Venezuelan Equine Encephalitis virus.

5. The method of claim 1, wherein said measurement of enzyme activities is carried out in a 96 well-plate.

* * * * *